United States Patent [19]

Tanaka et al.

[11] Patent Number: 4,626,384
[45] Date of Patent: Dec. 2, 1986

[54] PENAM DERIVATIVES

[75] Inventors: Motoaki Tanaka; Makoto Kajitani; Tomio Yamazaki, all of Tokushima, Japan

[73] Assignee: Taiho Pharmaceutical Company, Limited, Tokyo, Japan

[21] Appl. No.: 716,948

[22] Filed: Mar. 28, 1985

[30] Foreign Application Priority Data

Apr. 6, 1984 [JP] Japan .................................. 59-69843

[51] Int. Cl.$^4$ .................... C07D 499/32; A61K 31/43
[52] U.S. Cl. ....................................................540/306
[58] Field of Search ................ 260/245.2 R, 245.2 T, 260/239.5; 514/192, 195

[56] References Cited

U.S. PATENT DOCUMENTS 4,540,687 9/1985 Rellegg ........................ 260/245.2 R
4,562,073 12/1985 Micetich et al. ............. 260/245.2 R

FOREIGN PATENT DOCUMENTS 0097446 2/1982 European Pat. Off. .
0059046 6/1983 European Pat. Off. .

OTHER PUBLICATIONS

Chemical Abstracts, vol. 101, No. 23, 3rd Dec. 1984, p. 624, No. 210852j, Columbus, Ohio US; & JP-A-59 95 291 (Taiho Pharmaceutical Co., Ltd.) 01-06-1984.

*Primary Examiner*—Nicholas S. Rizzo
*Attorney, Agent, or Firm*—Murray and Whisenhunt

[57] ABSTRACT

This invention provides a penam derivative represented by the formula

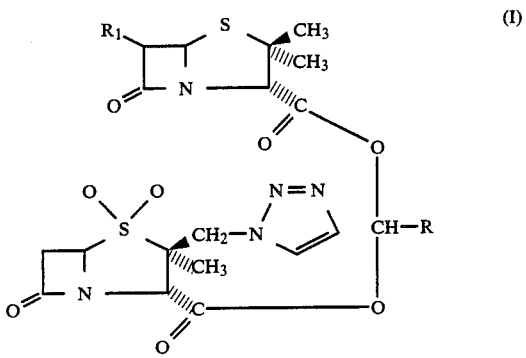

wherein R is hydrogen or methyl and $R_1$ is (hexahydro-1H-azepin-1-yl)methyleneamino, 2-phenylacetamido, 2-phenoxyacetamido, 2-amino-2-phenylacetamido, 2-amino-2-(p-hydroxyphenyl)acetamido or 2-(4-ethyl-2,3-dioxo-1-piperazine)carboxamido-2-phenylacetamido, and a salt thereof, and processes for preparing them.

8 Claims, No Drawings

PENAM DERIVATIVES

This invention relates to novel penam derivatives and salts thereof, and more particularly to novel penam derivatives and salts thereof having antimicrobial activity against β-lactam-producing microorganisms. This invention also concerns with processes for preparing the foregoing penam derivatives and salts thereof.

Of the commercially available antibiotics, β-lactam antibiotics having a β-lactam ring, namely penicillins and cephalosporins, are best known and frequently used. Although widely used as useful chemotherapeutic drugs, the β-lactam antibiotics can not achieve satisfactory effects against some types of microorganisms because of resistance of the microorganism to the β-lactam antibiotics. The resistance thereof is usually attributable to β-lactamase produced by the microorganism. The β-lactamase is an enzyme which acts to cleave the β-lactam ring of the β-lactam antibiotics, thereby causing the antibiotic to lose its antimicrobial activity. For this reason, the action of β-lactamase must be eliminated or inhibited so as to enable the β-lactam antibiotic to produce satisfactory effects. The elimination or inhibition of the β-lactamase activity can be achieved by β-lactamase inhibitors, which are used conjointly with the β-lactam antibiotic to increase the antimicrobial activity of the antibiotic.

It is known that compounds represented by the formula

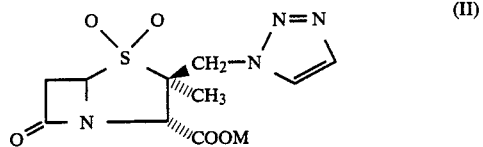

wherein M represents hydrogen atom or metal atom possess a β-lactamase inhibitory action. The compounds of the formula (II) are disclosed in European Patent Publication No. 97446 published on Jan. 4, 1984.

In the course of our research, we conceived the idea that if it is possible to link the compound of the formula (II) having β-lactamase inhibitory action with a β-lactam antibiotic, the resulting product may have antimicrobial activity, particularly against microorganisms resistant to β-lactam antibiotics. This concept has matured into the present invention.

This invention provides penam derivatives represented by the formula

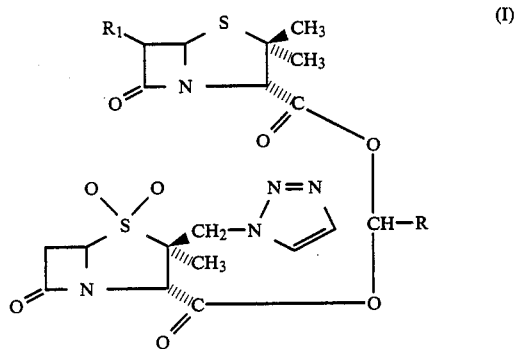

wherein R is hydrogen or methyl and $R_1$ is (hexahydro-1H-azepin-1-yl)methyleneamino, 2-phenylacetamido, 2-phenoxyacetamido, 2-amino-2-phenylacetamido, 2-amino-2-(p-hydroxyphenyl)acetamido or 2-(4-ethyl-2,3-dioxo-1-piperazine)carboxamido-2-phenylacetamido, and salts thereof.

The penam derivatives of the formula (I) and salts thereof are novel compounds which exhibit antimicrobial action against, among other microorganisms, those capable of producing β-lactamase. Preferable of the compounds of the formula (I) are:

(1) 6β-{(hexahydro-1H-azepin-1-yl)methyleneamino}-2,2-dimethylpenam-3α-carbonyloxymethyl 2'α-methyl-2'β-(1,2,3-triazol-1-yl)methylpenam-3'α-carboxylate 1',1'-dioxide;

(2) 1-{(6β-[(hexahydro-1H-azepin-1-yl)methyleneamino]-2,2-dimethylpenam-3α-carbonyloxy}ethyl 2'α-methyl-2'β-(1,2,3-triazol-1-yl)methylpenam-3'α-carboxylate 1',1'-dioxide;

(3) 6β-(2-phenylacetamido)-2,2-dimethylpenam-3α-carbonyloxymethyl 2'α-methyl-2'β-(1,2,3-triazol-1-yl)methylpenam-3'α-carboxylate 1',1'-dioxide;

(4) 6β-(2-phenoxyacetamido)-2,2-dimethylpenam-3α-carbonyloxymethyl 2'α-methyl-2'β-(1,2,3-triazol-1-yl)methylpenam-3'α-carboxylate 1',1'-dioxide;

(5) 6β-(2-amino-2-phenylacetamido)-2,2-dimethylpenam-3α-carbonyloxymethyl 2'α-methyl-2'β-(1,2,3-triazol-1-yl)methylpenam-3'α-carboxylate 1',1'-dioxide;

(6) 1-[6β-(2-amino-2-phenylacetamido)-2,2-dimethylpenam-3α-carbonyloxy]ethyl 2'α-methyl-2'β-(1,2,3-triazol-1-yl)methylpenam-3'α-carboxylate 1',1'-dioxide;

(7) 6β-[2-amino-2-(p-hydroxyphenyl)acetamido]-2,2-dimethylpenam-3α-carbonyloxymethyl 2'α-methyl-2'β-(1,2,3-triazol-1-yl)methylpenam-3'α-carboxylate 1',1'-dioxide;

(8) 1-{6β-[2-amino-2-(p-hydroxyphenyl)acetamido]-2,2-dimethylpenam-3α-carbonyloxy}ethyl 2'α-methyl-2'β-(1,2,3-triazol-1-yl)methylpenam-3'α-carboxylate 1',1'-dioxide;

(9) 6β-{2-[(4-ethyl-2,3-dioxo-1-piperazine)carboxamido]-2-phenylacetamido}-2,2-dimethylpenam-3α-carbonyloxymethyl 2'α-methyl-2'β-(1,2,3-triazol-1-yl)methylpenam-3'α-carboxylate 1',1'-dioxide.

The salts of the compounds of the formula (I) include pharmaceutically acceptable salts. Examples of such pharmaceutically acceptable salts are salts of inorganic acids such as hydrochloric acid, hydrobromic acid, hydriodic acid, phosphoric acid, sulfuric acid, nitric acid, etc.; salts of organic acids such as citric acid, benzenesulfonic acid, p-toluenesulfonic acid, naphthalenesulfonic acid, tartaric acid, acetic acid, maleic acid, etc.; and other pharmaceutically acceptable salts commonly used in the antibiotics art. These salts can be easily formed in the conventional manner. Examples of metal atoms represented by M in the compound of the formula (II) are alkali metal atoms such as sodium atom, potassium atom, etc.

The penam derivatives (I) of the present invention can be prepared, for example, by the following processes.

PROCESS A

As illustrated in the following reaction equation, a compound of the formula (III) is reacted with a compound of the formula (IV).

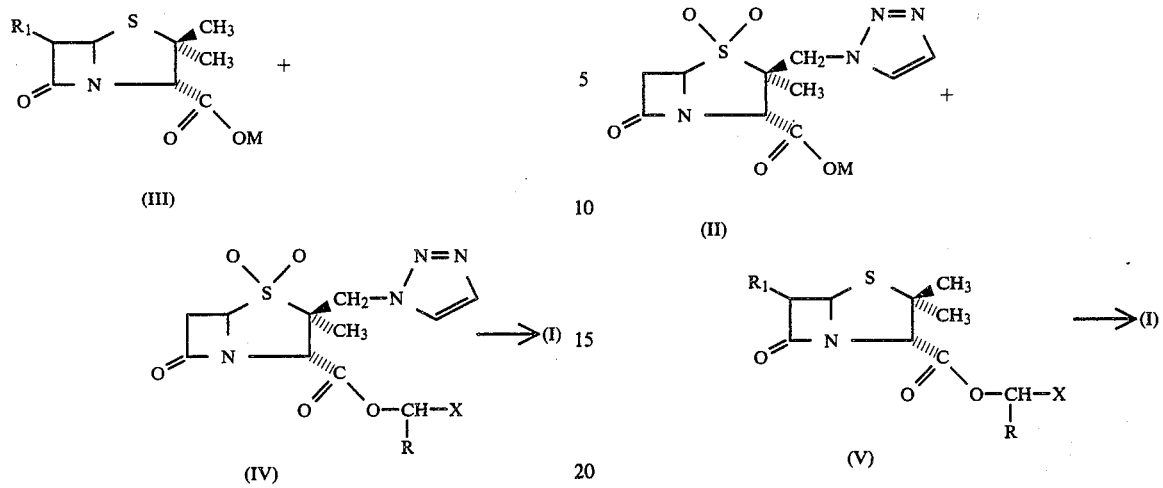

(III)

(IV)

In the foregoing formulas, R, R₁ and M are as defined above and X is halogen.

Examples of the halogen atoms represented by X are bromine atom, chlorine atom, iodine atom, etc. The reaction is carried out usually in a solvent. Useful solvents are not limited to particular kinds insofar as they do not adversely affect the reaction. Preferred examples thereof are polar organic solvents such as dimethylformamide, dimethylacetamide, dimethylsulfoxide. These polar organic solvents in mixture with a small amount of water are also preferred. The amount of water as mixed with the solvent is not particularly limited, but genarally ranges from 1 to 10% by volume of the polar organic solvents. Alkali can be used as a reaction accelerator in the foregoing reaction. Examples of useful alkali are weakly alkaline inorganic salts such as hydrogencarbonates of alkali metals, e.g., potassium hydrogencarbonate, sodium hydrogencarbonate; carbonates of alkali metals such as sodium carbonate, potassium carbonate, etc. While the proportions of the compounds of the formulas (III) and (IV) and the reaction accelerator used are not particularly limited, the reaction smoothly proceeds if they are used in equimolar amounts. The reaction is conducted at a temperature ranging from 0° C. to around room temperature and is generally complete in about 2 to about 5 hours. If desired, the resulting compound of the formula (I) can be reacted with an organic or inorganic acid in a conventional manner to prepare a salt thereof. The compounds of the formula (III) to be used as one of the starting materials are known compounds. The compounds of the formula (IV) serving as one of the starting materials are novel compounds, but can be easily prepared, for example, from the compound (II). The process for preparing the compound of the formula (IV) will be described later in Reference Examples.

PROCESS B

As shown in the following reaction scheme, a compound of the formula (II) is reacted with a compound of the formula (V).

(II)

(V)

In the foregoing formulas, R, R₁, M and X are as defined above.

The compounds of the formula (V) used in the above reaction scheme are known compounds, for example, as disclosed in Japanese Unexamined Patent Publication No. 113791/1980. The process for preparing the compound of the formula (II) is described in European Patent Publication No. 97446 and will also be shown later in Reference Examples.

The reaction conditions of Process B are the same as those of Process A and the reaction of Process B is carred out in the same manner as in Process A. More specifically, the reaction in Process B is effected in a solvent, such as the polar organic solvents as exemplified above and mixtures of such solvents with water. The alkalis as exemplified above, preferably weakly alkaline inorganic salts, may also be used as the reaction accelerator. Preferably the compounds of the formulas (II) and (V) and the reaction accelerator are used in equimolar amounts. The reaction is performed at a temperature ranging from 0° C. to room temperature and is complete in about 2 to about 5 hours. The resulting compound of the formula (I) may be reacted with the organic or inorganic acid in a conventional manner to prepare a salt thereof.

The compound of the present invention obtained by these processes can be separated from the reaction product and purified by conventional methods such as recrystallization, extraction and the like.

For use as antimicrobial agents, the penam derivatives of the formula (I) or salts thereof can be formulated into pharmaceutical compositions in the desired dosage form. The pharmaceutical compositions containing the present compound are useful for treating infections in mammals, particularly humans. These pharmaceutical compositions can take dosage forms such as tablets, powders, syrups, troches, solutions, suspensions and the like for oral mode of administration, or such as aqueous, suspending or water-soluble preparations for intravenous, intramuscular and subcutaneous injections.

Carriers useful for formulating the preparations are commonly used pharmaceutically acceptable non-toxic carriers such as lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. for oral preparations, and water, physiological saline solution, tris(hydroxymethyl)-aminomethane, sodium carbonate, sodium bicarbonate, sodium hydroxide, etc. for parenteral preparations. The carrier may be used with other conventional additives such as diluents, binders, buffers, preservatives, glazes, disintegrators, coating agents, etc.

The daily dose of the preparation can be suitably determined and may depend on age, weight and response of the individual patient, as well as the nature and the severity of the patient's symptoms. However, this judgement is well within the skill of the medical art. The amount is usually decided based on the antimicrobially effective amount of the compound of the formula (I). Preferably the daily dose is about 20 to about 300 mg/kg body weight for oral administration and about 5 to about 200 mg/kg body weight for parenteral administration.

The present invention will be described below in more detail with reference to Reference Examples showing the preparation of starting materials for the present compounds and Examples indicating the preparation of the present compounds.

REFERENCE EXAMPLE 1

Preparation of p-nitrobenzyl 2α-methyl-2β-(1,2,3-triazol-1-yl)methylpenam-3α-carboxylate 1,1-dioxide A 1.02 g quantity of p-nitrobenzyl 2β-azidomethyl-2α-methylpenam-3α-carboxylate 1,1-dioxide was reacted with 50 ml of vinyl acetate in a sealed tube at 100° to 110° C. for 30 hours. The reaction mixture was concentrated under reduced pressure and the residue was subjected to silica gel column chromatography, giving 0.73 g of an amorphous product. M.p. 182°–184° C.

Yield 67%.

IR spectrum (KBr): $\nu$max $(cm^{-1})=1800, 1760$.

NMR spectrum (CDCl$_3$): δ (ppm)=1.26 (3H, s), 3.5–3.6 (2H, m), 4.66 (1H, s), 4.6–4.7 (1H, m), 5.07 (2H, s), 5.36 (2H, s), 7.61 (2H, d), 7.74 (1H, d), 7.80 (1H, d), 8.28 (2H, d).

REFERENCE EXAMPLE 2

Preparation of sodium 2α-methyl-2β-(1,2,3-triazol-1-yl)methylpenam-3α-carboxylate 1,1-dioxide (compound of the formula (II), M=Na)

To 120 ml of ethyl acetate and 120 ml of water were added 5.22 g of p-nitrobenzyl 2α-methyl-2β-(1,2,3-triazol-1-yl)methylpenam-3α-carboxylate 1,1-dioxide, 1.20 g of 10% palladium carbon and 2.02 g of sodium hydrogencarbonate. The mixture was hydrogenated at room temperature. After completion of hydrogen absorption, the reaction mixture was filtered and the aqueous layer was separated and washed with benzene. The resulting aqueous solution was concentrated under reduced pressure and the concentrate was subjected to silica gel column chromatography using MCI gel, CHP-20 P (product of Mitsubishi Chemical Industries Limited, Japan) to conduct gradient elution with water-10% acetone in water. The eluate thus obtained was lyophilized, giving 3.09 g of the title compound as white powder which decomposed at or above 170° C.

Yield 80%.

IR spectrum (KBr): $\nu$max $(cm^{-1})=1780, 1630$.

NMR spectrum (D$_2$O): δ (ppm)=1.41 (3H, s), 3.45 (1H, dd), 3.72 (1H, dd), 4.48 (1H, s), 4.96–5.10 (1H, m), 5.14 (1H, d), 5.38 (1H, d), 7.85 (1H, d), 8.13 (1H, d).

REFERENCE EXAMPLE 3

Preparation of 2α-methyl-2β-(1,2,3-triazol-1-yl)methylpenam-3α-carboxylic acid 1,1-dioxide (compound of the formula (II), M=H)

A 6.58 g quantity of sodium 2α-methyl-2β-(1,2,3-triazol-1-yl)methylpenam-3α-carboxylate 1,1-dioxide was dissolved in water. The solution was adjusted to a pH of 1.7 with hydrochloric acid. The precipitated crystals were filtered, washed with water and then with ether and dried, giving 4.50 g of the title compound as white crystals.

Yield 73%.

M.p. 136°–138° C.

IR spectrum (KBr): $\nu$max $(cm^{-1})=1800, 1725$.

NMR spectrum (DMSO-d$_6$): δ (ppm)=1.34 (3H, s), 3.30 (1H, dd), 3.72 (1H, dd), 4.79 (1H, s), 4.90 (1H, d), 5.20 (1H, m), 5.25 (1H, d), 7.78 (1H, d), 8.09 (1H, d), 14.1 (1H, bs).

REFERENCE EXAMPLE 4

Preparation of chloromethyl 2α-methyl-2β-(1,2,3-triazol-1-yl)methylpenam-3α-carboxylate 1,1-dioxide (compound of the formula (IV), R=H, X=Cl)

A 1.34 quantity of sodium hydrogencarbonate and 0.124 g of tetrabutylammonium hydrogensulfate were added to a solution of 1.20 g of 2α-methyl-2β-(1,2,3-triazol-1-yl)methylpenam-3α-carboxylic acid 1,1-dioxide in 6.5 ml of dichloromethane and 6.5 ml of water. Thereto was added dropwise 0.779 g of chloromethyl chlorosulfonate, and the mixture was stirred at room temperature for 30 minutes. The organic layer was separated and the aqueous layer was extracted with dichloromethane. The organic layers were combined and purified by silica gel column chromatography, giving 0.757 g of the title compound as an amorphous product.

Yield 55%.

IR spectrum (KBr): $\nu$max $(cm^{-1})=1790$.

NMR spectrum (CDCl$_3$): δ (ppm)=1.44 (3H, s), 3.55–3.61 (2H, m), 4.67–4.73 (1H, m), 4.68 (1H, s), 5.09 (2H, s), 5.73 (1H, d), 5.91 (1H, d), 7.76 (1H, d), 7.82 (1H, d).

REFERENCE EXAMPLE 5

Preparation of iodomethyl 2α-methyl-2β-(1,2,3-triazol-1-yl)methylpenam-3α-carboxylate 1,1-dioxide (compound of the formula (IV), R=H, X=I)

To 1.6 ml of acetone were added 0.75 g of chloromethyl 2α-methyl-2β-(1,2,3-triazol-1-yl)-methylpenam-3α-carboxylate 1,1-dioxide and 0.68 g of sodium iodide, and the mixture was stirred at room temperature for 18 hours. To the reaction mixture was added 1.5 ml of water and the mixture was adjusted to a pH of 7 to 8 with an aqueous solution of sodium hydrogencarbonate. Thereto was added 1.5 ml of water and the mixture was decolored with a 0.5M aqueous solution of sodium thiosulfate and extracted with dichloromethane. The organic layer was washed with water and dried over magnesium sulfate. The solvent was distilled off, giving 0.63 g of the title compound as an amorphous product which decomposed at 128° to 142° C.

Yield 66%.

IR spectrum (KBr): νmax (cm$^{-1}$)=1790.

NMR spectrum (CDCl$_3$): δ (ppm)=1.46 (3H, s), 3.42–3.60 (2H, m), 4.74–4.84 (1H, m), 4.79 (1H, s), 5.10 (2H, s), 5.96 (1H, d), 6.08 (1H, d), 7.75 (1H, d), 7.89 (1H, d).

EXAMPLE 1

Preparation of
6β-{(hexahydro-1H-azepin-1-yl)methyleneamino}-2,2-dimethylpenam-3α-carbonyloxymethyl
2'α-methyl-2'β-(1,2,3-triazol-1-yl)methylpenam-3'α-carboxylate 1',1'-dioxide hydrochloride (Process A)

To 1.0 ml of dimethylformamide and 0.025 ml of water were added 0.145 g of mecillinam and 0.045 g of potassium hydrogencarbonate, and the mixture was stirred at or below 5° C. Thereto was added 0.17 g of iodomethyl 2α-methyl-2β-(1,2,3-triazol-1-yl)methylpenam-3α-carboxylate 1,1-dioxide, and the mixture was stirred at the same temperature for 3 hours. To the reaction mixture was added 2.6 ml of ethyl acetate and the mixture was washed twice with ice water (1.5 ml×2). Thereto was added 2 ml of ice water and the mixture was adjusted to a pH of 2 to 3 with hydrochloric acid. The aqueous layer was separated and saturated with sodium chloride, and the mixture was extracted twice with dichloromethane. The organic layer was dried over magnesium sulfate. The solvent was distilled off and the residue was dissolved in water. The solution was lyophilized, giving 0.13 g of the title compound as white powder. M.p. 132°–136° C.

IR spectrum (KBr): νmax (cm$^{-1}$)=1790, 1685.

NMR spectrum (D$_2$O): δ (ppm)=1.47 (3H, s), 1.55 (3H, s), 1.74 (3H, s), 1.5–2.0 (8H, m), 3.4–3.9 (6H, m), 5.0–5.2 (4H, m), 5.28 (1H, s), 5.51 (1H, d), 5.56 (1H, d), 6.02 (2H, m), 7.87 (1H, d), 8.03 (1H, s), 8.13 (1H, d).

EXAMPLE 2

Preparation of
1-[6β-{(hexahydro-1H-azepin-1-yl)methyleneamino}-2,2-dimethylpenam-3α-carbonyloxy]ethyl
2'α-methyl-2'β-(1,2,3-triazol-1-yl)methylpenam-3'α-carboxylate 1',1'-dioxide hydrochloride The general procedure of Example 1 was repeated using iodoethyl 2α-methyl-2β-(1,2,3-triazol-1-yl)methylpenam-3α-carboxylate 1,1-dioxide in place of the 1-iodomethyl 2α-methyl-2β-(1,2,3-triazol-1-yl)methylpenam-3α-carboxylate 1,1-dioxide, thereby producing the title compound.

EXAMPLE 3

Preparation of
6β-{(hexahydro-1H-azepin-1-yl)methyleneamino}-2,2-dimethylpenam-3α-carbonyloxymethyl
2'α-methyl-2'β-(1,2,3-triazol-1-yl)methylpenam-3'α-carboxylate 1',1'-dioxide hydrochloride (Process B)

A 0.54 g quantity of sodium 2α-methyl-2β-(1,2,3-triazol-1-yl)methylpenam-3α-carboxylate 1,1-dioxide was added to a solution of 0.81 g of iodomethyl 6-[(hexahydro-1H-azepin-1-yl)methylene-amino]-penicillanate in 20 ml of dimethylformamide. The mixture was stirred at room temperature for 1 hour. To the reaction mixture was added 30 ml of ethyl acetate and the mixture was washed twice with ice water (3 ml×2). Thereto was added 4 ml of ice water and the mixture was adjusted to a pH of 2 to 3 with hydrochloric acid (0.5N). The aqueous layer was separated and saturated with sodium chloride. The mixture was extracted with dichloromethane twice and the organic layer was dried over magnesium sulfate. The solvent was distilled off under reduced pressure and the residue was dissolved in water. The solution was lyophilized, giving 0.50 g of the title compound as white powder, M.p. 132°–136° C.

The IR spectrum data and NMR spectrum data of the product thus obtained were identical with those of the compound prepared in Example 1.

EXAMPLE 4

Preparation of
6β-(2-amino-2-phenylacetamido)-2,2-dimethylpenam-3α-carbonyloxymethyl
2'α-methyl-2'β-(1,2,3-triazol-1-yl)methylpenam-3'α-carboxylate 1',1'-dioxide hydrochloride To 1.0 ml of dimethylformamide and 0.025 ml of water were added 0.230 g of ampicillin and 0.057 g of potassium hydrogencarbonate, and the mixture was stirred at or below 5° C. Thereto was added 0.210 mg of iodomethyl 2α-methyl-2β-(1,2,3-triazol-1-yl)methylpenam-3α-carboxylate 1,1-dioxide and the mixture was stirred at the same temperature for 2 hours. To the reaction mixture was added 2.6 ml of ethyl acetate and the mixture was washed with ice water (1.5 ml×2). Thereto was added 2 ml of ice water and the mixture was adjusted to a pH of 2 to 3 with hydrochloride acid. The aqueous layer was separated and saturated with sodium chloride. The mixture was extracted with dichloromethane twice and the organic layer was dried over magnesium sulfate. The solvent was distilled off, the residue was dissolved in water and the solution was lyophilized, giving the title compound.

IR spectrum (KBr): νmax (cm$^{-1}$)=1790, 1690.

NMR spectrum (DMSO-d$_6$): δ (ppm)=1.34 (3H, s), 1.38 (3H, bs), 1.46 (3H, s), 3.2–3.9 (2H, m), 4.43 (1H, s), 5.09 (1H, s), 4.7–5.6 (6H, m), 5.88 (2H, bs), 7.1–7.6 (5H, m), 7.78 (1H, d), 8.09 (1H, d), 8.5–9.1 (2H, bs), 9.41 (1H, d).

EXAMPLE 5

Preparation of
6β-{2-amino-2-(p-hydroxyphenyl)acetamido}-2,2-dimethylpenam-3α-carbonyloxymethyl
2'α-methyl-2'β-(1,2,3-triazol-1-yl)methylpenam-3'α-carboxylate 1',1'-dioxide hydrochloride The general procedure of Example 4 was repeated using amoxicillin in place of the ampicillin employed in Example 4, thereby producing the title compound.

IR spectrum (KBr): νmax (cm$^{-1}$)=1795, 1685.

NMR spectrum (DMSO-d$_6$): δ (ppm)=1.34 (3H, s), 1.44 (3H, s), 1.47 (3H, s), 3.25–3.9 (2H, m), 4.42 (1H, s), 4.81 (1H, s), 4.7–5.6 (6H, m), 5.88 (2H, bs), 6.74 (2H, d), 7.24 (2H, d), 7.79 (2H, d), 8.09 (1H, d), 8.7–9.4 (2H, bs), 9.30 (1H, bs).

EXAMPLE 6

Preparation of
6β-(2-phenylacetamido)-2,2-dimethylpenam-3α-carbonyloxymethyl
2'α-methyl-2'β-(1,2,3-triazol-1-yl)methylpenam-3'α-carboxylate 1',1'-dioxide To 1.0 ml of dimethylformamide and 0.02 ml of water were added 0.20 g of benzylpenicillin and 0.056 g of potassium hydrogencarbonate, and the mixture was stirred at or below 5° C. To the mixture was added 0.22 g of iodomethyl 2α-methyl-2β-(1,2,3-triazol-1-yl)methylpenam-3α-carboxylate 1,1-dioxide and the mixture was stirred at 25° C. for 8 hours. After completion of the reaction, the reaction mixture was washed twice with ice water (1.5 ml×2). Thereto was added 3 ml of ice water and the mixture was adjusted to a pH of 8.5. The resulting mixture was extracted with ethyl acetate and the ethyl acetate layer was washed with water and dried over anhydrous sodium sulfate. The solvent was distilled off and the residue was subjected to column chromatography, giving the title compound.

EXAMPLE 7

Preparation of 6β-(2-phenoxyacetamido)-2,2-dimethylpenam-3α-carbonyloxymethyl-2'α-methyl-2'β-(1,2,3-triazol-1-yl)methylpenam-3'α-carboxylate 1',1'-dioxide hydrochloride The general procedure of Example 4 was repeated using 6β-phenoxyacetamidopenicillin in place of the ampicillin employed in Example 4, thereby producing the title compound.

Given below were examples of antimicrobial compositions containing the present compound.

| Preparation Example 1 | |
|---|---|
| Compound prepared in Example 1 | 200 mg |
| Lactose | 100 mg |
| Crystalline cellulose | 57 mg |
| Magnesium stearate | 3 mg |
| 1 capsule | 360 mg |

The above ingredients were formulated in the proportions listed above into a capsule.

| Preparation Example 2 | |
|---|---|
| Compound prepared in Example 4 | 200 mg |
| Lactose | 300 mg |
| Corn starch | 490 mg |
| Hydroxypropylmethyl cellulose | 10 mg |
| granules | 1000 mg |

The above ingredients were formulated in the proportions as listed above into granules.

| Preparation Example 3 | |
|---|---|
| Compound prepared in Example 5 | 100 mg |
| Crystalline cellulose | 25 mg |
| Magnesium stearate | 10 mg |
| Talc | 5 mg |
| Corn starach | 15 mg |
| Hydroxypropylmethyl cellulose | 10 mg |
| Lactose | 35 mg |
| 1 tablet | 200 mg |

The above ingredients were formulated in the proportions listed above into a tablet.

We claim:
1. A penam derivative represented by the formula

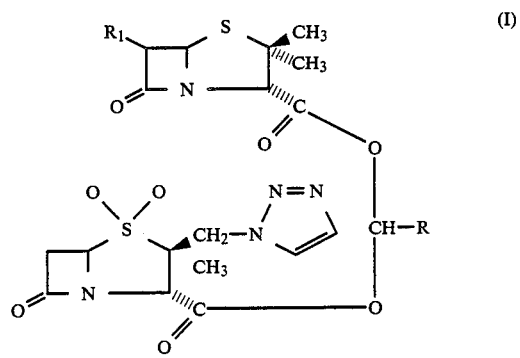

wherein R is hydrogen or methyl and $R_1$ is (hexahydro-1H-azepin-1-yl)methyleneamino, 2-phenylacetamido, 2-phenoxyacetamido, 2-amino-2-phenylacetamido, 2-amino-2-(p-hydroxyphenyl)acetamido or 2-(4-ethyl-2,3-dioxo-1-piperazine)carboxamido-2-phenylacetamido, or a pharmaceutically acceptable salt thereof.

2. A compound as defined in claim 1 wherein R is hydrogen.

3. A compound as defined in claim 1 wherein R is methyl.

4. A compound as defined in claim 1 wherein $R_1$ is (hexahydro-1H-azepin-1-yl)methyleneamino.

5. A compound as defined in claim 1 wherein $R_1$ is 2-amino-2-phenylacetamido.

6. A compound as defined in claim 1 wherein $R_1$ is 2-amino-2-(p-hydroxyphenyl)acetamido.

7. A compound as defined in claim 1 wherein $R_1$ is 2-phenylacetamido.

8. A compound as defined in claim 1 wherein $R_1$ is phenoxyacetamido.

* * * * *